United States Patent
Farmer et al.

(10) Patent No.: US 11,932,891 B2
(45) Date of Patent: Mar. 19, 2024

(54) **CO-CULTURE OF MYXOBACTERIA AND *BACILLUS* FOR ENHANCED METABOLITE PRODUCTION**

(71) Applicant: Locus Solutions IPCo, LLC, Solon, OH (US)

(72) Inventors: Sean Farmer, Ft. Lauderdale, FL (US); Ken Alibek, Solon, OH (US); Yajie Chen, Solon, OH (US)

(73) Assignee: LOCUS SOLUTIONS IPCO, LLC, Solon, OH (US)

( * ) Notice: Subject to any disclaimer, the term of this patent is extended or adjusted under 35 U.S.C. 154(b) by 167 days.

(21) Appl. No.: 17/439,600

(22) PCT Filed: Mar. 31, 2020

(86) PCT No.: PCT/US2020/025877
§ 371 (c)(1),
(2) Date: Sep. 15, 2021

(87) PCT Pub. No.: WO2020/205815
PCT Pub. Date: Oct. 8, 2020

(65) Prior Publication Data
US 2022/0154238 A1 May 19, 2022

Related U.S. Application Data

(60) Provisional application No. 62/867,053, filed on Jun. 26, 2019, provisional application No. 62/835,780, filed on Apr. 18, 2019, provisional application No. 62/827,305, filed on Apr. 1, 2019.

(51) Int. Cl.
| | |
|---|---|
| *C12P 21/02* | (2006.01) |
| *C12N 1/20* | (2006.01) |
| *C12N 1/34* | (2006.01) |
| *C12P 7/6436* | (2022.01) |
| *C12P 19/00* | (2006.01) |
| *C12P 39/00* | (2006.01) |

(52) U.S. Cl.
CPC ........... *C12P 21/02* (2013.01); *C12N 1/20* (2013.01); *C12N 1/34* (2013.01); *C12P 7/6436* (2013.01); *C12P 19/00* (2013.01); *C12P 39/00* (2013.01)

(58) Field of Classification Search
CPC ......... C12P 21/02; C12P 39/00; C12P 7/6436; C12N 1/20; C12N 1/34
See application file for complete search history.

(56) References Cited

U.S. PATENT DOCUMENTS

2018/0272396 A1    9/2018   Farmer et al.

FOREIGN PATENT DOCUMENTS

WO    WO-2018049182 A2 *   3/2018   ............ A01N 63/00

OTHER PUBLICATIONS

Müller, Susanne, et al. "Bacillaene and sporulation protect Bacillus subtilis from predation by Myxococcus xanthus." Applied and environmental microbiology 80.18 (2014): 5603-5610. (Year: 2014).*
Wei, Yu-Hong, Li-Fen Wang, and Jo-Shu Chang. "Optimizing iron supplement strategies for enhanced surfactin production with Bacillus subtilis." Biotechnology Progress 20.3 (2004): 979-983. (Year: 2004).*
Pérez, Juana, et al. "Development versus predation: Transcriptomic changes during the lifecycle of Myxococcus xanthus." Frontiers in Microbiology 13 (2022): 1004476. (Year: 2022).*
Winterburn, J. B., and P. J. Martin. "Foam mitigation and exploitation in biosurfactant production." Biotechnology letters 34 (2012): 187-195. (Year: 2012).*
Mueller, S., et al., "Bacillaene and Sporulation Protect Bacillus subtilis from Predation by Myxococcus xanthus." Applied and Environmental Microbiology, 2014, 80(18): 5603-5610.
Mueller, S., et al., "Identification of Functions Affecting Predator-Prey Interactions between Myxococcus xanthus and Bacillus subtilis." Journal of Bacteriology, 2016, 198(24): 3335-3344.
Mueller, S., et al., "Predation by Myxococcus xanthus Induces Bacillus subtilis to Form Spore-Filled Megastructures." Applied and Environmental Microbiology, 2015, 81(1): 203-210.
Perez, J., et al., "Myxoccus xanthus Induces Actinorhodin Overproduction and Aerial Mycelium Formation by Streptomyces coelicolor." Microbial Biotechnology, 2011, 4(2): 175-183.
Liu, X., et al., "Optimization for the Production of Surfactin with a New Synergistic Antifungal Activity." PLoS One, May 2012, 7(5): e34430, pp. 1-9.
Sarwar, A., et al., "Qualitative analysis of biosurfactants from *bacillus* species exhibiting antifungal activity." PLoS One, 2018, 13(6): e0198107, pp. 1-15.
Wang, C., et al., "Bacillus licheniformis escapes from Myxococcus xanthus predation by deactivating myxovirescin A through enzymatic glucosylation." Environmental Microbiology, 2019, 21(12): 4755-4772.

* cited by examiner

*Primary Examiner* — Robert J Yamasaki
*Assistant Examiner* — Trevor Kane
(74) *Attorney, Agent, or Firm* — SALIWANCHIK, LLOYD & EISENSCHENK

(57) ABSTRACT

The subject invention provides microbe-based products and efficient methods of producing them. In specific embodiments, methods are provided for enhanced production of microbial biosurfactants, the methods comprising co-cultivating *Myxococcus xanthus* and *Bacillus amyloliquefaciens*. In preferred embodiments, co-cultivation is carried out continuously for an indefinite period of time. Microbe-based products produced according to the subject methods are also provided, as well as their uses in, for example, agriculture, oil and gas recovery, and health care.

14 Claims, No Drawings

CO-CULTURE OF MYXOBACTERIA AND *BACILLUS* FOR ENHANCED METABOLITE PRODUCTION

CROSS-REFERENCE TO RELATED APPLICATIONS

This application is a National Stage Application of International Application No. PCT/US2020/025877, filed Mar. 31, 2020; which claims priority to U.S. Provisional Patent Application No. 62/827,305, filed Apr. 1, 2019; No. 62/835,780, filed Apr. 18, 2019; and No. 62/867,053, filed Jun. 26, 2019, each of which is incorporated by reference herein in its entirety.

BACKGROUND OF THE INVENTION

Cultivation of microorganisms such as bacteria, yeast and fungi is important for the production of a wide variety of useful bio-preparations. Microorganisms play crucial roles in, for example, food industries, pharmaceuticals, agriculture, oil and gas recovery, mining, environmental remediation, and waste management; however, one of the factors restricting commercialization of microbe-based products has been the cost per propagule density, as it is particularly expensive and unfeasible to produce microbes and their growth by-products on a large scale.

Interest in microbial surfactants, i.e., biosurfactants, in particular, has been steadily increasing in recent years due to their structural diversity, environmental-friendliness, selectivity, performance under extreme conditions, and potential "green" applications in various industries.

Biosurfactants are a structurally diverse group of surface-active substances produced by microorganisms. All biosurfactants are amphiphiles consisting of two parts: a polar (hydrophilic) moiety and non-polar (hydrophobic) group. The hydrocarbon chain of a fatty acid acts as the common hydrophobic moiety of a biosurfactant molecule, whereas the hydrophilic part can be formed by, for example, esters, alcohols, carboxylates, amino acids, peptides and/or carbohydrates. Due to their amphiphilic structure, biosurfactants can, for example, increase the surface area of hydrophobic water-insoluble substances, increase the water bioavailability of such substances, and change the properties of bacterial cell surfaces.

Biosurfactants can also reduce the interfacial tension between water and oil and, therefore, lower the hydrostatic pressure required to move entrapped liquid to overcome the capillary effect. Biosurfactants accumulate at interfaces, thus reducing interfacial tension and leading to the formation of aggregated micellar structures in solution. The formation of micelles provides a physical mechanism to mobilize, for example, oil in a moving aqueous phase. The ability of biosurfactants to form pores and destabilize biological membranes also permits their use as antibacterial, antifungal, and hemolytic agents to, for example, control pest and/or microbial growth.

There are multiple types of biosurfactants, which include glycolipids, lipopeptides, flavolipids, phospholipids, fatty acid esters, and high molecular weight polymers such as lipoproteins, lipopolysaccharide-protein complexes, and polysaccharide-protein-fatty acid complexes.

Lipopeptides, in particular, are oligopeptides synthesized by bacteria using large multi-enzyme complexes. They are frequently used as antibiotic compounds, and exhibit a wide antimicrobial spectrum of action, in addition to surfactant activities. All lipopeptides share a common cyclic structure consisting of a β-amino or β-hydroxy fatty acid integrated into a peptide moiety.

Many strains of *Bacillus* spp. bacteria are capable of producing lipopeptides, for example, *Bacillus amyloliquefaciens*; however, only a low concentration can be produced per batch (e.g., 0.5 to 1 g/L) with current known production methods, and production typically halts after only one day of fermentation.

The most commonly studied family of lipopeptides, the surfactin family, consists of heptapeptides containing a β-hydroxy fatty acid with 13 to 15 carbon atoms. Surfactins are considered some of the most powerful biosurfactants. They are capable of some antiviral activity, as well as antifungal activity, and they exhibit strong synergy when used in combination with another lipopeptide, iturin A. Furthermore, surfactins may also be a key factor in the establishment of stable biofilms, while also inhibiting the biofilm formation of other bacteria, including Gram-negative bacteria.

The fengycin family, which includes plipastatins, are decapeptides with a β-hydroxy fatty acid. Fengycins exhibit some unusual properties, such as the presence of ornithine in the peptide portion. They are capable of antifungal activity, although more specific for filamentous fungi.

The iturin family, represented by, e.g., iturin A, mycosubtilin, and bacillomycin, are heptapeptides with a β-amino fatty acid. Iturins also exhibit strong antifungal activity.

Other lipopeptides have been identified, which exhibit a variety of useful characteristics. These include, but are not limited to, kurstakins, arthrofactin, viscosin, glomosporin, amphisin, and syringomycin, to name a few.

Another important class of biosurfactants are glycolipids, which include, for example, sophorolipids, mannosylerythritol lipids and rhamnolipids. In general, glycolipids are lipids with a carbohydrate attached by a glycosidic bond. Due in part to their amphiphilic structure, glycolipids have excellent surface and interfacial tension reduction properties, as well as other beneficial biochemical properties that are useful in applications such as enhanced oil recovery (EOR), agriculture, cosmetics, household products, as well as the health, medical and pharmaceutical fields.

Sophorolipids are glycolipids that consist of a disaccharide sophorose linked to a long chain hydroxy fatty acid. They have a partially acetylated 2-O-β-D-glucopyranosyl-D-glucopyranose unit attached β-glycosidically to 17-L-hydroxyoctadecanoic or 17-L-hydroxy-Δ9-octadecenoic acid. The hydroxy fatty acid is generally 16 or 18 carbon atoms, and may contain one or more unsaturated bonds. The fatty acid carboxyl group can be free (acidic or open form) or internally esterified at the 4"-position (lactone form).

Mannosylerythritol lipids (MEL) comprise either 4-O-B-D-mannopyranosyl-meso-erythritol or 1-O-B-D-mannopyranosyl-meso-erythritol as the hydrophilic moiety, and fatty acid groups and/or acetyl groups as the hydrophobic moiety. In some instances, one or two hydroxyls, typically at the C4 and/or C6 of the mannose residue, can be acetylated. Furthermore, there can be one to three esterified fatty acids, from 8 to 12 carbons or more in chain length.

Rhamnolipids comprise a rhamnose moiety and a 3-(hydroxyalkanoyloxy)alkanoic acid fatty acid tail. Two main classes of rhamnolipids exist, mono-rhamnolipids and di-rhamnolipids, which have one or two rhamnose groups, respectively. The length and degree of branching in the fatty acid tail can also vary between rhamnolipid molecules.

There exists an enormous potential for the use of both lipopeptides and glycolipids, as well as other microbial-produced amphiphilic molecules, in a broad range of industries. However, production on an industrial scale can be costly, and current methods do not allow for the production of these products in the amounts needed for such large scale applications. Thus, improved methods are needed for producing biosurfactants, particularly lipopeptides, with greater efficiency and on a large scale.

BRIEF SUMMARY OF THE INVENTION

The subject invention provides methods of producing microorganisms and their growth by-products. More specifically, the subject invention provides for enhanced methods of producing microbial biosurfactants and other useful microbial metabolites. Advantageously, the microbe-based products and methods of the subject invention are environmentally-friendly, operational-friendly and cost-effective.

In preferred embodiments, the subject invention provides methods for producing one or more microbial growth by-products, the methods comprising co-cultivating a myxobacterium and a *Bacillus* spp. bacterium. Advantageously, in certain embodiments, the methods can be carried out indefinitely without halting cultivation or production of growth by-products. Additionally, in certain embodiments, the total cell biomass and/or the total production of the one or more growth by-products achieved when using the subject methods is greater than when pure cultures of the individual microbes are cultivated on their own, and/or than when using non-continuous methods.

In certain preferred embodiments, methods for co-cultivating microorganisms and/or for production of microbial growth by-products are provided, the methods comprising inoculating a fermentation system comprising liquid growth medium with a first microorganism and inoculating the fermentation system with a second microorganism, wherein the first microorganism is a *Myxococcus* spp. bacterium and the second microorganism is a *Bacillus* spp. bacterium.

In one embodiment, the *Myxococcus* is *M. xanthus* and the *Bacillus* is, for example, *B. amyloliquefaciens*, *B. cereus*, *B. firmus*, *B. laterosporus*, *B. licheniformis*, *B. megaterium*, and/or *B. subtilis*. In certain embodiments, more than one *Bacillus* sp. can be included. In preferred embodiments, a strain of *B. amyloliquefaciens* is used, for example, NRRL B-67928.

In one embodiment, the microorganisms are co-cultivated using cultivation processes ranging from small to large scale. These cultivation processes can include, but are not limited to, submerged cultivation/fermentation, solid state fermentation (SSF), and hybrids, modifications and/or combinations thereof. In preferred embodiments, the cultivation process is continuous.

In one embodiment, co-cultivation utilizes a liquid growth medium, comprising sources of, for example, carbon, nitrogen, proteins, vitamins and/or minerals. In certain embodiments, the nutrient medium is customized for production of desired biosurfactants and/or other metabolites.

In certain embodiments, the medium comprises carbohydrates, e.g., glucose, powdered molasses and/or sucrose; inorganic salts, e.g., potassium phosphate, monopotassium phosphate, dipotassium phosphate, sodium phosphate, potassium chloride, magnesium sulfate, sodium chloride, manganese chloride, calcium carbonate, calcium nitrate and/or calcium chloride; nitrogen sources, e.g., urea, and/or ammonium chloride; and/or sources of vitamins, minerals and/or proteins, e.g., peptone, yeast extract and/or trace elements.

In certain embodiments, the methods utilize a hybrid of SSF and submerged fermentation, wherein a particulate anchoring carrier is suspended in the liquid culture medium to serve as a site for cell attachment and/or biofilm formation. This is particularly useful for the growth of myxobacteria, which can exhibit enhanced growth on a solid surface.

In some embodiments, the particulate anchoring carrier is suspended in the liquid culture medium prior to, concurrently with, or after the liquid culture medium is inoculated with the first and/or second microorganisms.

In one embodiment, the anchoring carrier can be any sterilized material suitable for serving as a nucleation site for bacterial attachment and growth. In some embodiments, the material comprises a plurality of individual fine particles, e.g., grains, that are about 0.1 μm to about 5 mm in diameter. Bacteria can attach to the particles and accumulate thereon, producing bacterial-carrier masses.

The anchoring carrier can be inert, or it can carry and/or comprise additional nutrients and/or microbial inoculant. In certain embodiments, the anchoring carrier can be porous. The anchoring carrier can comprise synthetic materials and/or naturally-derived materials.

In one embodiment, the anchoring carrier comprises balls made of, for example, glass, a polymer (e.g., polylactic acid (PLA)), agar, or gelatin. In one embodiment, the anchoring carrier can be pieces of, for example, a cut-up sponge or loofa. In one embodiment, the anchoring carrier can comprise, for example, whole, or pieces of, seeds, nuts, beans or even pieces of chopped fruit, such as bananas.

In preferred embodiments, the anchoring carrier comprises fine grains of cellulose (e.g., powdered cellulose) and/or corn flour (e.g., nixtamilized corn flour).

Advantageously, the use of the anchoring carrier provides for increased production of bacterial biomass due to, for example, the increased surface area to which the bacteria can attach and accumulate. Additionally, the accumulation of bacterial biomass can lead to increases in the production of beneficial growth by-products, such as biosurfactants and other secondary metabolites.

In one embodiment, bacteria grow in the form of a biofilm on the particulate anchoring carrier. In one embodiment, some bacteria grow in planktonic form the liquid culture medium and some bacteria grow on the particulate anchoring carrier. In certain embodiments, the first and the second microorganisms are capable of growing in either biofilm or planktonic form, and may grow in one or both forms during co-cultivation.

According to the subject methods, the first and second microorganisms can be incubated in the fermentation system for a time period sufficient to achieve a desired effect, e.g., production of a desired amount of cell biomass or a desired amount of one or more microbial growth by-products. In some embodiments, fermentation occurs for 24 hours or longer, at a temperature of 20 to 30° C.

In one embodiment, the process is continuous, where the growth by-product(s) of interest is/are collected from the culture, for example, from a foam that forms during co-cultivation. The microbial cells remain in the culture and the nutrient medium is replenished to continue microbial growth and production of metabolites until, for example, foam is no longer being produced by the process. The collected foam can be processed by, for example, washing and/or centrifuging to extract the microbial growth by-product(s).

In preferred embodiment, the methods of the subject invention can be used to produce one or more microbial growth by-products, wherein the growth by-products are biosurfactants.

Biosurfactants according to the subject invention can include, for example, glycolipids, lipopeptides, flavolipids, phospholipids, high-molecular-weight polymers, fatty acid esters, fatty acid ethers, lipoproteins, lipopolysaccharide-protein complexes, and/or polysaccharide-protein-fatty acid complexes.

In specific embodiments, the one or more biosurfactants are lipopeptides, such as, e.g., surfactin, iturin, lichenysin, fengycin, plipastatins, kurstakins, arthrofactin, and/or viscosin. In certain embodiments, the methods can be used to produce from 5 to 30 g/L of lipopeptides.

In certain embodiments, more than one type of biosurfactant is produced during co-cultivation, for example, glycolipids, and/or fatty acid esters may be produced in addition to the lipopeptides.

In some embodiments, the one or more growth by-products can also include other metabolites, for example, enzymes, biopolymers, acids, solvents, gases, proteins, peptides, amino acids, alcohols, hormones, lipids, carbohydrates, antibiotics, other organic compounds and/or other bioactive compounds.

Advantageously, in certain embodiments, the methods of the subject invention can result in the production of biosurfactants and/or other growth by-products at greater concentrations than when pure cultures of the individual microbes are cultivated separately. Furthermore, the subject methods can be carried out for longer periods of time than standard cultivation of Bacillus spp. for production of biosurfactants, which can typically only occur for about 24 hours.

In certain embodiments, the subject invention provides microbe-based products produced according to the subject methods, as well as their uses in, for example, improved oil production, bioremediation and mining; waste disposal and treatment; human health and pharmaceutical products; promoting plant health and productivity; and reclaiming and/or restoring the health of soils.

The microbe-based products can comprise the entire culture produced according to the subject methods, including the first and/or the second microorganisms and/or their growth by-products, as well as residual growth medium, foam, particulate anchoring carrier and/or nutrients.

The microorganisms can be live, viable or in an inactive form. They can be in the form of a biofilm, vegetative cells, spores, and/or a combination thereof. In certain embodiments, no microbes are present, wherein the composition comprises microbial growth by-products, e.g., biosurfactants, that have been extracted from the culture and, optionally, purified.

DETAILED DESCRIPTION

The subject invention provides methods of producing microorganisms and their growth by-products. Advantageously, the microbe-based products and methods of the subject invention are environmentally-friendly, operational-friendly and cost-effective.

In preferred embodiments, the subject invention provides methods for enhanced production of one or more microbial growth by-products, the methods comprising co-cultivating a myxobacterium and a Bacillus spp. bacterium. In certain preferred embodiments, the methods provide for continuous co-cultivation and production of microbial growth by-products In a specific embodiment, the growth by-products include biosurfactants. Even more specifically, in certain embodiments, the biosurfactants are lipopeptides.

The growth by-products can also include other metabolites, for example, enzymes, biopolymers, acids, solvents, gases, proteins, peptides, amino acids, alcohols, hormones, lipids, carbohydrates, antibiotics, other organic compounds and other bioactive compounds.

Advantageously, the total cell biomass and/or the total production of the one or more growth by-products achieved according to the separately. Furthermore, the subject methods can be carried out for longer periods of time than standard methods of cultivating Bacillus spp. for production of bio surfactants.

Selected Definitions

As used herein, a "bioflilm" is a complex aggregate of microorganisms, such as bacteria, wherein the cells adhere to each other and/or to a surface using an extracellular polysaccharide matrix. The cells in biofilms are physiologically distinct from planktonic cells of the same organism, which are single cells that can float or swim in liquid medium.

As used herein, "co-cultivation" means cultivation of more than one strain or species of microorganism in a single fermentation system. In some instances, the microorganisms interact with one another, either antagonistically or symbiotically, resulting in a desired effect, e.g., a desired amount of cell biomass growth or a desired amount of metabolite production. In one embodiment, this antagonistic or symbiotic relationship can result in an enhanced effect, for example, the desired effect can be magnified when compared to what results from cultivating only one of the chosen microorganisms on its own. In an exemplary embodiment, one microorganism causes and/or stimulates the production of one or more metabolites by another microorganism, e.g., a Myxococcus sp. stimulates a Bacillus sp. to produce a biosurfactant.

As used herein, "enhancing" refers to improving and/or increasing.

As used herein, "fermentation" refers to cultivation or growth of cells under controlled conditions. The growth could be aerobic or anaerobic.

As used herein, an "isolated" or "purified" molecule or other compound is substantially free of other compounds, such as cellular material, with which it is associated in nature. For example, a purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. A purified or isolated microbial strain is removed from the environment in which it exists in nature. Thus, the isolated strain may exist as, for example, a biologically pure culture, or as spores (or other forms of the strain) in association with a carrier.

In certain embodiments, purified compounds are at least 60% by weight the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state or in spore form, or a mixture of both. The microbes may be planktonic or in a biofilm form, or a mixture of both. The by-products of growth may be, for example, metabolites (e.g., biosurfactants), cell membrane components, expressed proteins, and/or other cellular components. The microbes may be intact or lysed. The cells or spores may be totally absent, or present at, for example, a concentration of at least $1\times10^4$, $1\times10^5$, $1\times10^6$, $1\times10^7$, $1\times10^8$, $1\times10^9$, $1\times10^{10}$, $1\times10^{11}$ or $1\times10^{12}$ or more CFU per milliliter of the composition.

The subject invention further provides "microbe-based products," which are products that are to be applied in practice to achieve a desired result. The microbe-based product can be simply the microbe-based composition harvested from the microbe co-cultivation process. Alternatively, the microbe-based product may comprise further ingredients that have been added. These additional ingredients can include, for example, stabilizers, buffers, carriers (e.g., water or salt solutions), added nutrients to support further microbial growth, non-nutrient growth enhancers and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, "reduces" means a negative alteration of at least 1%, 5%, 10%, 25%, 50%, 75%, or 100%.

As used herein, "surfactant" means a compound that lowers the surface tension (or interfacial tension) between two liquids, between a gas and a liquid, or between a liquid and a solid. Surfactants act as, e.g., detergents, wetting agents, emulsifiers, foaming agents, and/or dispersants. A "biosurfactant" is a surface-active substance produced by a living cell.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. Use of the term "comprising" contemplates other embodiments that "consist" or "consist essentially" of the recited components(s).

Unless specifically stated or obvious from context, as used herein, the term "or" is understood to be inclusive. Unless specifically stated or obvious from context, as used herein, the terms "a," "and," and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. All references cited herein are hereby incorporated by reference.

Methods of Co-Cultivation

The subject invention provides materials and methods for the production of biomass (e.g., viable or inactive cellular material), extracellular metabolites, and/or intracellular components. In preferred embodiments, the subject invention provides improved methods for producing one or more microbial growth by-products, wherein the methods comprise co-cultivating two or more different microorganisms in a fermentation reactor.

Advantageously, the total cell biomass and/or the total production of the one or more growth by-products achieved when using the subject co-cultivation methods can be greater compared to when cultures of the individual microbes are cultivated separately. Furthermore, the subject methods can be carried out for longer periods of time than standard methods of cultivating *Bacillus* spp. for production of biosurfactants.

More specifically, in preferred embodiments, the subject invention provides methods for enhanced production of one or more microbial growth by-products, the method comprising co-cultivating a first microorganism and a second microorganism in a submerged fermentation reactor under conditions favorable for growth and production of the one or more growth by-products. In certain embodiments, the first microorganism is a myxobacterium and the second microorganism is a *Bacillus* spp. bacterium.

In one embodiment, the microorganisms are co-cultivated using cultivation systems ranging from small to large scale. These cultivation systems can include, but are not limited to, submerged cultivation/fermentation, solid state fermentation (SSF), and hybrids, modifications and/or combinations thereof.

In certain preferred embodiments, the methods for co-cultivating microorganisms and/or for producing microbial growth by-products comprise inoculating a fermentation system comprising a liquid nutrient medium with a first microorganism and inoculating the fermentation system with a second microorganism, wherein the first microorganism is a *Myxococcus* spp. bacterium and the second microorganism is a *Bacillus* spp. bacterium. Even more preferably, in one embodiment, the *Myxococcus* is *M. xanthus* and the *Bacillus* is *B. amyloliquefaciens*.

In a certain embodiment, the *B. amyloliquefaciens* is strain NRRL B-67928.

The microbe growth vessel used according to the subject invention can be any fermenter or cultivation reactor for industrial use. In one embodiment, the vessel may have functional controls/sensors or may be connected to functional controls/sensors to measure important factors in the co-cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, samples may be taken at any point throughout fermentation in order to perform, e.g., CFU count, sporulation percentage and/or purity measurements. In one embodiment, sampling is performed at the start of fermentation, and multiple times per day (e.g., twice per day) throughout fermentation.

In one embodiment, the fermentation reactor is fitted with or connected to a feed tank. The feed tank can hold liquid nutrient medium for feeding into the fermentation reactor. In certain embodiments, the nutrient medium is fed into the fermentation reactor continuously, e.g., at a consistent rate from the start of fermentation until fermentation is halted. In other embodiments, the nutrient medium is fed into the fermentation reactor only when needed (e.g., when foam production slows or stops, or when sporulation percentage is measured at 20% or greater).

In one embodiment, the fermentation reactor is fitted with or connected to a collection container. In one embodiment, the collection container is separated from the fermentation reactor. Foam produced during cultivation can be extracted from the culture and placed into the collection container, either manually or using, for example, piping. Because, in certain embodiments, the foam contains microbial growth by-products that are sensitive to changes in pH, the collection container may be fitted with a pH sensor to measure pH of the foam so that it can be adjusted if necessary. For example, in some embodiments, the desired pH range for the foam is about 2.0 to 3.0. The metabolites present in the foam can be analyzed using, for example, LC-MS.

In certain embodiments, the co-cultivation method utilizes submerged fermentation. In certain embodiments, a hybrid of solid state and submerged fermentation is used, wherein a particulate anchoring carrier is suspended in the liquid culture medium to serve as a site for cell attachment and biofilm formation. This is particularly useful for the growth of myxobacteria, which can exhibit enhanced growth on a solid surface or other carrier.

In one embodiment, the liquid nutrient medium comprises a carbon source. The carbon source can be a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, rice bran oil, olive oil, corn oil, sesame oil, canola oil and/or linseed oil; powdered molasses, etc. These carbon sources may be used independently or in a combination of two or more.

In one embodiment, the liquid nutrient medium comprises a nitrogen source. The nitrogen source can be, for example, potassium nitrate, ammonium nitrate, ammonium sulfate, ammonium phosphate, ammonia, urea, and/or ammonium chloride. These nitrogen sources may be used independently or in a combination of two or more.

In one embodiment, one or more inorganic salts may also be included in the liquid nutrient medium. Inorganic salts can include, for example, potassium dihydrogen phosphate, monopotassium phosphate, dipotassium hydrogen phosphate, disodium hydrogen phosphate, potassium chloride, magnesium sulfate, magnesium chloride, iron sulfate, iron chloride, manganese sulfate, manganese chloride, zinc sulfate, lead chloride, copper sulfate, calcium chloride, calcium carbonate, calcium nitrate, magnesium sulfate, sodium phosphate, sodium chloride, and/or sodium carbonate. These inorganic salts may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, proteins and microelements can be included, for example, peptone, yeast extract, potato extract, beef extract, soybean extract, banana peel extract, and the like, or in purified forms. Amino acids such as, for example, those useful for biosynthesis of proteins, can also be included.

In some embodiments, the particulate anchoring carrier is suspended in the liquid culture medium prior to, concurrently with, or after the liquid culture medium is inoculated with the first and/or second microorganisms.

The particulate anchoring carrier can be any material suitable for serving as a nucleation site for bacterial attachment and/or biofilm formation. In some embodiments, the material comprises a plurality of individual pieces, particles, and/or grains, that are about 0.1 μm to about 5 mm, about 0.2 μm to about 4 mm, about 0.3 μm to about 3 mm, about 0.4 μm to about 2 mm, about 0.5 μm to about 1 mm, or about 1 μm to about 0.5 mm in diameter. Bacteria will attach to the pieces and accumulate thereon, producing bacterial-carrier masses.

The anchoring carrier can be inert, or it can carry and/or comprise additional nutrients and/or microbial inoculant. In certain embodiments, the anchoring carrier can be porous. The anchoring carrier can comprise synthetic materials and/or naturally-derived materials.

In one embodiment, the anchoring carrier comprises sodium alginate beads. The beads can be prepared by, for example, continuously adding a solution comprising 1 to 5%, or 2 to 3% aseptic sodium alginate and, optionally, nutrients and/or bacterial inoculant, into a sterile 1 to 7%, or 2 to 5% calcium chloride solution to form beads.

In one embodiment, the anchoring carrier can comprise balls made of, for example, glass, a polymer (e.g., polylactic acid (PLA)), agar, or gelatin. In one embodiment, the anchoring carrier can be pieces of, for example, a chopped sponge or loofa. In one embodiment, the anchoring carrier can comprise, for example, whole, or pieces of, seeds, nuts, beans or even pieces of chopped fruit, such as bananas.

In preferred embodiments, the anchoring carrier comprises fine grains of cellulose (e.g., powdered cellulose) and/or corn flour (e.g., nixtamilized corn flour). In one embodiment, the use of fine grains (e.g., 0.1 μm to 5 mm) is preferred over larger particles because it facilitates scaling-up of the process.

Advantageously, the use of the anchoring carrier provides for increased production of bacterial biomass due to, for example, the increased surface area to which the bacteria can attach and accumulate. Additionally, the accumulation of bacterial biomass can lead to increases in the production of beneficial growth by-products, such as biosurfactants.

In one embodiment, bacteria grow in the form of a biofilm on the anchoring carrier. In one embodiment, some bacteria grow in the liquid culture medium in planktonic form, and some bacteria grow on the anchoring carrier. Either or both of the first and the second microorganism can grow in biofilm and/or planktonic form.

In some embodiments, the liquid culture medium is inoculated with the microorganisms prior to, or concurrently with, suspension of the anchoring carrier. In some embodiments, the anchoring carrier is pre-inoculated with the first and/or second microorganism before being suspended in the liquid culture medium.

The method of co-cultivation can further provide oxygenation to the growing culture. One embodiment utilizes slow motion of air to remove low-oxygen containing air and introduce oxygenated air. The oxygenated air may be ambient air supplemented daily through mechanisms including impellers for mechanical agitation of the liquid, and air spargers for supplying bubbles of gas to the liquid for dissolution of oxygen into the liquid. In certain embodiments, dissolved oxygen (DO) levels are maintained at about 25% to about 75%, about 30% to about 70%, about 35% to about 65%, about 40% to about 60%, or about 50% of air saturation. Air flow can be supplied at, for example, about 0.5 to about 2.0 v/m, or about 1.0 to about 1.5 vvm.

In some embodiments, the method for co-cultivation may further comprise adding additional acids and/or antimicrobials in the liquid medium before and/or during the co-cultivation process for protecting the culture against contamination.

In one embodiment, prior to inoculation, the components of the liquid culture medium can optionally be sterilized. If used, the anchoring carrier is also preferably sterilized, for example, using an autoclave or other method known in the art. Additionally, water used for preparing the medium can be filtered to prevent contamination.

In one embodiment, sterilization of the liquid nutrient medium can be achieved by placing the components of the liquid culture medium in water at a temperature of about 85-100° C. In one embodiment, sterilization can be achieved by dissolving the components in 1 to 3% hydrogen peroxide in a ratio of 1:3 (w/v).

In one embodiment, the equipment used for co-cultivation is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of pH and/or low water activity may be exploited to control unwanted microbial growth.

The pH of the mixture should be suitable for the microorganism of interest. In some embodiments, the pH is about 2.0 to about 11.0, about 3.0 to about 10.0, about 4.0 to about 9.0, about 5.0 to about 8.0, or about 6.0 to about 7.0. In one embodiment, the pH is about 6.8. Buffers, and pH regulators, such as carbonates and phosphates, may be used to stabilize pH near a preferred value. When metal ions are present in high concentrations, use of a chelating agent in the liquid medium may be necessary.

In one embodiment, the method for co-cultivation of microorganisms is carried out at about 5° to about 100° C., about 15° to about 60° C., about 20° to about 45° C., or about 24° to about 30° C. In one embodiment, the co-cultivation may be carried out continuously at a constant temperature. In another embodiment, the co-cultivation may be subject to changing temperatures.

According to the subject methods, the first and second microorganisms can be incubated in the fermentation system for a time period sufficient to achieve a desired effect, e.g., production of a desired amount of cell biomass or a desired amount of one or more microbial growth by-products. The biomass content may be, for example, from 5 g/l to 180 g/l or more, or from 10 g/l to 150 g/l.

The microbial growth by-product(s) produced by the first and/or second microorganisms may be retained in the microorganisms or secreted into the growth medium. In certain embodiments, the growth by-product(s) form a foam layer at the top of the culture.

In another embodiment, the method for producing microbial growth by-products may further comprise steps of extracting, concentrating and/or purifying the microbial growth by-product of interest. Alternatively, the microbial growth by-products can be utilized in their crude form, meaning no purification is performed. In a further embodiment, the growth medium may contain compounds that stabilize the activity of the microbial growth by-product.

In some embodiments, fermentation occurs for 24 hours to 1 week or, preferably, longer. The methods can be performed in a batch, quasi-continuous, or continuous processes. In preferred embodiments, the process is continuous, with the potential to be carried out indefinitely as long as nutrient medium is replenished and favorable conditions for growth and product of microbial growth by-products are maintained within the reactor.

In one embodiment, all of the foam, nutrient medium, cells and/or bacterial-carrier masses are removed upon the completion of the co-cultivation (e.g., upon, for example, achieving a desired cell density, or amount of metabolite-containing foam). The remaining cell mass can be recycled and/or hydrolyzed to obtain any leftover compounds present in the cells. In this batch procedure, an entirely new batch is initiated upon harvesting of the first batch.

In one embodiment, the process is continuous or quasi-continuous, where the growth by-products of interest are collected from the culture, for example, from the foam that forms during co-cultivation and/or from the liquid nutrient medium. In preferred embodiments, the foam and/or medium is placed into a collection container with an optional pH meter. Biomass and/or inoculated anchoring carriers with viable cells remain in the fermentation reactor as an inoculant and the nutrient medium is replenished, e.g., from a feed tank housing fresh nutrient medium, to continue microbial growth and production of metabolites.

In one embodiment, the foam can be extracted on a consistent basis, meaning every 1 to 24 hours, every other day, or every 2 to 7 days. In another embodiment, the foam can be extracted upon reaching a certain volume, for example, upon reaching a pre-determined height within the fermentation reactor. The composition that is removed can be a cell-free foam or broth, and/or it can contain some cells.

Foam and/or broth that is collected from the fermentation reactor can be processed by, e.g., washing and/or centrifuging to extract the microbial growth by-products. Optionally, the growth by-products can then be stored, purified, and/or used directly in crude form.

In one embodiment, some or all of the anchoring carrier, if used, can be harvested from the culture and washed using a solvent, for example, low concentration (e.g., 1 to 2%) ethanol. The resulting liquid is then centrifuged to separate growth by-products and cell mass.

Advantageously, the total cell biomass and/or the total production of the one or more growth by-products achieved when using the subject co-cultivation methods can be greater compared to when pure cultures of the individual microbes are cultivated on their own.

In certain embodiments, the total cell biomass achieved according to the subject methods is at least 0.01%, 1%, 5%, 10%, 20%, 30%, 40%, 50%, 60%, 70%, 80%, 90%, 100%, or more, greater than when the first and second microorganisms are cultivated individually.

In certain embodiments, the total concentration of a growth by-product produced according to the subject methods is at least 0.01%, 1%, 5%, 10%, 20%, 30%, 40%, 50%, 60%, 70%, 80%, 90%, 100%, or more, greater than when the first and second microorganisms are cultivated individually.

Microbial Strains Grown in Accordance with the Subject Invention

The microorganisms grown according to the systems and methods of the subject invention can be, for example, bacteria, yeast and/or fungi. These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In preferred embodiments, the microorganisms are bacteria, including Gram-positive and Gram-negative bacteria. In specific embodiments, the first microorganism is selected from myxobacteria. Myxobacteria are slime-forming, predatory bacteria that live in groups, or swarms. These swarms may form complex biofilms, as well as fruiting body structures, which are either simple or branched aggregates containing myxospores. During predation, the bacteria secrete predatory molecules, including enzymes, antibiotics and other secondary metabolites, which can include, for example, biosurfactants.

Myxobacteria include, for example, *Myxococcus* spp., *Stignatella aurantiaca*, *Sorangium cellulosum*, *Minicystis rosea*, and *Chondromyces crocatus*.

In preferred embodiments, the myxobacteria is a *Myxococcus* spp. bacterium selected from, for example, *M. xanthus*, *M. fulvus*, *M. flavescens*, *M. macrosporus*, *M. stipitatus*, *M. virescens*, *M. coralloides*, and *M. disciformis*. Even more preferably, the *Myxococcus* is *M. xanthus*.

In specific embodiments, the second microorganism is selected from *Bacillus* spp. bacteria. In general, *Bacillus* spp. bacteria are spore-forming, Gram-positive bacteria capable of producing valuable enzymes and biosurfactants. In preferred embodiments, the second microorganism is a *Bacillus* spp. such as, for example, *B. amyloliquefaciens*, *B. coagulans*, *B. firms*, *B. larvae*, *B. laterosporus*, *B lentimorbus*, *B. licheniformis*, *B. megaterium*, *B popilliae*, *B. polymyxa*, *B sphaericus*, *B. subtilis*, and/or *B. thuringiensis*.

In certain embodiments, one or more additional microorganisms is included, in addition to the first and second microorganisms. In some embodiments, the additional microorganism(s) are *Bacillus* spp. bacteria other than that which is utilized as the second microorganism.

In preferred embodiments, *M. xanthus* and *B. amyloliquefaciens* are co-cultivated according to the subject methods.

In a specific embodiment, the *B. amyloliquefaciens* is NRRL B-67928 ("*B. amy*"). A culture of the *B. amyloliquefaciens* "*B. amy*" microbe has been deposited with the Agricultural Research Service Northern Regional Research Laboratory (NRRL) Culture Collection, 1815 N. University St., Peoria, IL, USA. The deposit has been assigned accession number NRRL B-67928 by the depository and was deposited on Feb. 26, 2020.

The subject culture has been deposited under conditions that assure that access to the culture will be available during the pendency of this patent application to one determined by the Commissioner of Patents and Trademarks to be entitled thereto under 37 CFR 1.14 and 35 U.S.C 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

Advantageously, in some embodiments, the cell biomass from co-cultivation of these two microbes is greater than when pure cultures of the individual microbes are cultivated. Furthermore, in some embodiments, production of biosurfactants and/or other metabolites in co-culture is greater than when pure cultures of the individual microbes are used.

In certain embodiments, this enhanced production of growth by-products and/or metabolites is caused by the co-cultivation, wherein the presence of a competitor microorganism induces enhanced production of, for example, defensive molecules and/or self-growth promoters.

Microbial Growth by-Products

The methods of the subject invention can be used to produce compositions comprising one or more useful microbial growth by-products such as, for example, biosurfactants and/or other microbial metabolites.

In preferred embodiments, the growth by-products are one or more biosurfactants. Biosurfactants according to the subject invention can include, for example, glycolipids, lipopeptides, flavolipids, phospholipids, fatty acid esters, fatty acid ethers, lipoproteins, lipopolysaccharide-protein complexes, and/or polysaccharide-protein-fatty acid complexes.

In specific embodiments, the one or more biosurfactants are one or more lipopeptides, such as, e.g., surfactin, lichenysin, iturin, fengycin, plipastatin, arthrofactin, kurstakins, bacillomycin, mycosubtilin, glomosporin, amphisin, syringomycin and/or viscosin. In some embodiments, the biosurfactants are also useful and/or known as antibiotics. In certain embodiments, the methods can be used to produce from about 1 to about 30 g/L of lipopeptides, about 5 to about 20 g/L, or about 10 to about 15 g/L.

In some embodiments, the microorganisms can also produce one or more additional types of biosurfactants, such as glycolipids (e.g., rhamnolipids, sophorolipids, trehalose lipids, cellobiose lipids and/or mannosylerythritol lipids) and/or fatty acid esters (e.g., oleic fatty acid esters). In certain embodiments, the methods can be used to produce about 0.5 to about 10 g/L of the one or more additional types of biosurfactants, or about 1 to about 5 g/L.

In some embodiments, the microbial growth by-products include other metabolites. As used herein, a "metabolite" refers to any substance produced by metabolism (e.g., a growth by-product), or a substance necessary for taking part in a particular metabolic process, for example, enzymes, enzyme inhibitors, biopolymers, acids, solvents, gases, proteins, peptides, amino acids, alcohols, pigments, pheromones, hormones, lipids, ectotoxins, endotoxins, exotoxins, carbohydrates, antibiotics, anti-fungals, anti-virals and/or other bioactive compounds. The metabolite content produced by the method can be, for example, at least 0.1%, 1%, 5%, 10%, 20%, 30%, 40%, 50%, 60%, 70%, 80%, or 90%.

Enzymes according to the subject invention can include, for example, oxidoreductases, transferases, hydrolases, lyases, isomerases and/or ligases. Specific types and/or subclasses of enzymes according to the subject invention can also include, but are not limited to, nitrogenases, proteases, amylases, glycosidases, cellulases, glucosidases, glucanases, galactosidases, moannosidases, sucrases, dextranases, hydrolases, methyltransferases, phosphorylases, dehydrogenases (e.g., glucose dehydrogenase, alcohol dehydrogenase), oxygenases (e.g., alkane oxygenases, methane monooxygenases, dioxygenases), hydroxylases (e.g., alkane hydroxylase), esterases, lipases, ligninases, mannanases, oxidases, laccases, tyrosinases, cytochrome P450 enzymes, peroxidases (e.g., chloroperoxidase and other haloperoxidases), and lactases.

In certain embodiments, the one or more growth by-products include antibiotic compounds, such as, for example, aminoglycosides, amylocyclicin, bacitracin, bacillaene, bacilysin, bacilysocin, corallopyronin A, difficidin, etnangien gramicidin, β-lactams, lichenifonnin, macrolactinsublancin, oxydifficidin, plantazolicin, ripostatin, spectinomycin, subtilin, tyrocidine, and/or zwittermicin A. In some embodiments, an antibiotic can also be a type of biosurfactant.

In certain embodiments, the one or more growth by-products include anti-fungal compounds, such as, for example, fengycin, surfactin, haliangicin, mycobacillin, mycosubtilin, and/or bacillomycin. In some embodiments, an anti-fungal can also be a type of biosurfactant.

In certain embodiments, the one or more growth by-products include other bioactive compounds, such as, for example, butanol, ethanol, acetate, ethyl acetate, lactate, acetoin, benzoic acid, 2,3-butanediol, beta-glucan, indole-3-acetic acid (IAA), lovastatin, aurachin, kanosamine, reseoflavin, terpentecin, pentalenolactone, thuringiensin (β-exotoxin), polyketides (PKs), terpenes, terpenoids, phenyl-propanoids, alkaloids, siderophores, as well as ribosomally and non-ribosomally synthesized peptides, to name a few.

Microbe-Based Products

The subject invention provides microbe-based products, as well as their use in a variety of applications, including, for example, agriculture, enhanced oil recovery, bioremediation, pharmaceuticals, and cosmetics.

One microbe-based product of the subject invention is simply the fermentation medium containing the microorganisms, microbial growth by-products produced by the microorganisms, any residual nutrients and/or residual particulate anchoring carrier. One microbe-based product comprises the foam produced during cultivation, said foam comprising one or more microbial growth by-products. The foam product may be used with or without extraction and/or purification.

The microorganisms may be in an active or inactive form, or in the form of vegetative cells, biofilm, spores, or a combination thereof. In one embodiment, the first and second microorganisms are separated from each other after co-cultivation. In one embodiment, the product comprises a blend of the first and second microorganisms and/or their growth by-products.

In one embodiment, the composition does not comprise live microorganisms. In one embodiment, the composition does not comprise microorganisms at all, whether live or inactive.

In one embodiment, the composition comprises the one or more microbial growth by-products separated from the microorganism that produced them. The growth by-products can be in a purified or unpurified form.

The microorganisms in the microbe-based product may be in an active or inactive form. The microbe-based products may be used without further stabilization, preservation, and storage. Advantageously, direct usage of these microbe-based products preserves a high viability of the microorganisms, reduces the possibility of contamination from foreign agents and undesirable microorganisms, and maintains the activity of the by-products of microbial growth.

The microbes and/or foam resulting from the microbial growth can be removed from the fermenter and/or collection container and transferred via, for example, piping for immediate use.

In other embodiments, the composition (microbes, broth and/or foam) can be placed in containers of appropriate size, taking into consideration, for example, the intended use, the contemplated method of application, the size of the fermentation tank, and any mode of transportation from microbe growth facility to the location of use. Thus, the containers into which the microbe-based composition is placed may be, for example, from 1 gallon to 1,000 gallons or more. In certain embodiments the containers are 2 gallons, 5 gallons, 25 gallons, or larger.

Upon harvesting the microbe-based composition from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, tracking agents, pesticides, and other ingredients specific for an intended use.

Advantageously, in accordance with the subject invention, the microbe-based product may comprise broth in which the microbes were grown. The product may be, for example, at least, by weight, 1%, 5%, 10%, 25%, 50%, 75%, or 100% broth. The amount of biomass in the product, by weight, may be, for example, anywhere from 0% to 100% inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, the product is stored at or below a temperature such as, for example, 20° C., 15° C., 10° C., 5° C. or 4° C., or less. If cells are present and in spore form, the product is, in one embodiment, stored and transported at a low temperature, not higher than 15° C., in order to prevent premature germination.

Methods of Use

The compositions of the subject invention can be used for a variety of purposes. In one embodiment, the composition can be used in agriculture. For example, methods are provided wherein a composition produced according to the subject invention is applied to a plant and/or its environment to treat and/or prevent the spread of pests and/or diseases. The composition can also be useful for enhancing water dispersal and absorption in the soil, as well as enhance nutrient absorption from the soil through plant roots, facilitate plant health, increase yields, and manage soil aeration.

In one embodiment, the subject compositions can be highly advantageous in the context of the oil and gas industry. When applied to an oil well, wellbore, subterranean formation, or to equipment used for recovery oil and/or gas, the compositions produced according to the subject invention can be used in methods for enhancement of crude oil recovery; reduction of oil viscosity; removal and dispersal of paraffins and/or asphaltenes from rods, tubing, liners, and pumps; prevention of equipment corrosion; recovery of oil from oil sands and stripper wells; enhancement of fracking operations as fracturing fluids; reduction of $H_2S$ concentration in formations and crude oil; and cleaning of tanks, flowlines and pipelines.

In one embodiment, the compositions produced according to the subject invention can be used to improve one or more properties of oil. For example, methods are provided wherein the composition is applied to oil or to an oil-bearing formation in order to reduce the viscosity of the oil, convert the oil from sour to sweet oil, and/or to upgrade the oil from heavy crude into lighter fractions.

In one embodiment, the compositions produced according to the subject invention can be used to clean industrial equipment. For example, methods are provided wherein a composition is applied to oil production equipment such as an oil well rod, tubing and/or casing, to remove heavy hydrocarbons, paraffins, asphaltenes, scales and other contaminants from the equipment. The composition can also be applied to equipment used in other industries, for example, food processing and preparation, agriculture, paper milling, and others where fats, oils and greases build up and contaminate and/or foul the equipment.

In one embodiment, the compositions produced according to the subject invention can be used to enhance animal health. For example, methods are provided wherein the composition can be applied to animal feed or water, or mixed with the feed or water, and used to prevent the spread of disease in livestock and aquaculture operations, reduce the need for antibiotic use in large quantities, reduce methanogenesis in the animals digestive system, as well as to provide supplemental proteins and other nutrients.

In one embodiment, the compositions produced according to the subject invention can be used to prevent spoilage of food, prolong the consumable life of food, and/or to prevent food-borne illnesses. For example, methods are provided wherein the composition is applied to a food product, such as fresh produce, baked goods, meats, and post-harvest grains, to prevent undesirable microbial growth.

Other uses for the subject compositions include, but are not limited to, biofertilizers, biopesticides, bioleaching, bioremediation of soil and water, pharmaceutical adjuvants (e.g., for increasing bioavailability of orally ingested drugs), cosmetic products, control of unwanted microbial growth, and many others.

Local Production of Microbe-Based Products

In certain embodiments of the subject invention, a microbe growth facility produces fresh, high-density microorganisms and/or microbial growth by-products of interest on a desired scale. The microbe growth facility may be located at or near the site of application. The facility produces high-density microbe-based compositions in batch, quasi-continuous, or continuous cultivation.

The distributed microbe growth facilities can be located at the location where the microbe-based product will be used. For example, the microbe growth facility may be less than 300, 250, 200, 150, 100, 75, 50, 25, 15, 10, 5, 3, or 1 mile from the location of use.

The microbe growth facilities of the subject invention produces fresh, microbe-based compositions, comprising the microbes themselves, microbial metabolites, and/or other components of the broth in which the microbes are grown. If desired, the compositions can have a high density of vegetative cells or propagules, or a mixture of vegetative cells and propagules.

Because the microbe-based product is generated locally, without resort to the microorganism stabilization, preservation, storage and transportation processes of conventional microbial production, a much higher density of bacteria cells and/or propagules can be generated, thereby requiring a smaller volume of the microbe-based product for use in the on-site application or which allows much higher density microbial applications where necessary to achieve the desired efficacy. Local generation of the microbe-based product also facilitates the inclusion of the growth broth in the product. The broth can contain agents produced during the fermentation that are particularly well-suited for local use.

Advantageously, the compositions can be tailored for use at a specified location. The microbe growth facilities provide manufacturing versatility by the ability to tailor the microbe-based products to improve synergies with destination geographies and harness the power of naturally-occurring local microorganisms and their metabolic by-products to improve oil production. Local microbes can be identified based on, for example, salt tolerance and ability to grow at high temperatures.

Advantageously, these microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell-count product and the associated broth and metabolites in which the cells are originally grown.

The microbe-based products of the subject invention are particularly advantageous compared to traditional products wherein cells have been separated from metabolites and nutrients present in the fermentation growth media. Reduced transportation times allow for the production and delivery of fresh batches of microbes and/or their metabolites at the time and volume as required by local demand.

Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver microbe-based products.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1—Continuous Production of Lipopeptides

*Bacillus amyloliquefaciens* inoculum is grown in a small-scale reactor for 24 to 48 hours. *Myxococcus xanthus* inoculum is grown in a 2 L working volume seed culture flask for 48 to 120 hours. A fermentation reactor is inoculated with the two inocula. Nutrient medium is fed to the fermentation reactor continuously from a feed tank. The nutrient medium comprises:

| | |
|---|---|
| Glucose | 1 g/L to 5 g/L |
| Casein peptone | 1 g/L to 10 g/L |
| $K_2HPO_4$ | 0.01 g/L to 1.0 g/L |
| $KH_2PO_4$ | 0.01 g/L to 1.0 g/L |
| $MgSO_4 \cdot 7H_2O$ | 0.01 g/L to 1.0 g/L |
| NaCl | 0.01 g/L to 1.0 g/L |
| $CaCO_3$ | 0.5 g/L to 5 g/L |
| $Ca(NO_3)_2$ | 0.01 g/L to 1.0 g/L |
| Yeast extract | 0.01 g/L to 5 g/L |
| $MnCl_2 \cdot 4H_2O$ | 0.001 g/L to 0.5 g/L |
| Teknova trace element | 0.5 ml/L to 5 ml/L |

Fine grain particulate anchoring carrier is suspended in the nutrient medium. The carrier comprises cellulose (1.0 to 5.0 g/L) and/or corn flour (1.0 to 8.0 g/L).

pH in the reactor is maintained at about 6.8; temperature is maintained at about 24° C.; DO is maintained at about 50%; and air flow rate is maintained at about 1 vvm.

A foam layer comprising microbial growth by-products is produced during fermentation and is purged out and collected in a container comprising a pH meter. The pH meter is used to monitor the pH of the foam: if the pH varies outside of the range of 2.0 to 3.0, pH adjusters are added to bring the pH back within that range for long-term preservation of the lipopeptides therein. Foam continues to be produced, purged from the reactor, and collected for 7 days or longer (e.g., indefinitely).

Sampling of the fermenter and the foam collection tank for CFU count, sporulation percentage and/or purity is performed at 0 hr., then twice per day throughout fermentation. Sampling can also occur at the time that foam is purged and collected. When/if sporulation percentage of the bacterial culture is detected (using microscope slide estimation) to be greater than 20%, additional nutrient media is added to the fermenter. LC-MS analysis is carried out on acidified lipopeptide samples from the foam collection tank. The samples are stored at about 4° C.

The fermentation cycle is continued for at least one week, with nutrient medium feeding and foam collection occurring until, for example, foam can no longer be extracted from the fermenter.

The invention claimed is:

1. A method for enhanced production of one or more microbial growth by-products, the method comprising co-cultivating a first microorganism and a second microorganism in a fermentation reactor,
    wherein the first microorganism is a myxobacterium and the second microorganism is *B. amyloliquefaciens* NRRL B-67928, and
    wherein a greater concentration of the one or more microbial growth by-products is achieved than would be achieved if the first and second microorganisms were cultivated individually.

2. The method of claim 1, wherein the myxobacterium is a *Myxococcus* spp.

3. The method of claim 2, wherein the *Myxococcus* is *M. xanthus*.

4. The method of claim 1, wherein the one or more growth by-products are biosurfactants.

5. The method of claim 4, wherein the biosurfactants are lipopeptides.

6. The method of claim 5, wherein the lipopeptides are surfactin, iturin and/or fengycin.

7. The method of claim 5, wherein the biosurfactants are glycolipids and/or fatty acid esters.

8. The method of claim 1, wherein a greater cell biomass is achieved for the first and/or second microorganism than if the first and second microorganisms were cultivated separately.

9. The method of claim 1, wherein co-cultivating the first and the second microorganisms comprises:
    inoculating the fermentation reactor with the first microorganism and inoculating the fermentation reactor with the second microorganism, wherein the fermentation reactor comprises a liquid nutrient medium;
    incubating the first and second microorganisms under conditions favorable for growth and production of the one or more microbial growth by-products;
    extracting the one or more growth by-products from the reactor;
    collecting the one or more growth by-products in a collection container; and, optionally,
    purifying the one or more growth by-products.

10. The method of claim 9, wherein the liquid nutrient medium comprises a particulate anchoring carrier suspended therein as a site for nucleating microbial growth.

11. The method of claim 9, carried out continuously for 1 week or longer, wherein the one or more growth by-products are extracted and collected on a consistent basis, and wherein the liquid nutrient medium is continuously replenished.

12. The method of claim 9, wherein the one or more growth by-products are produced in the form of a foam layer.

13. The method of claim 1, wherein the first microorganism stimulates enhanced production of the one or more growth by-products by the second microorganism.

14. The method of claim 1, wherein the growth by-products are produced at a concentration that is at least 0.01% to at least 90% greater than if the first or the second microorganisms were cultivated separately.

* * * * *